April 18, 1972 W. L. STAGGS ET AL Plant Pat. 3,127
PEACH TREE
Filed June 14, 1967
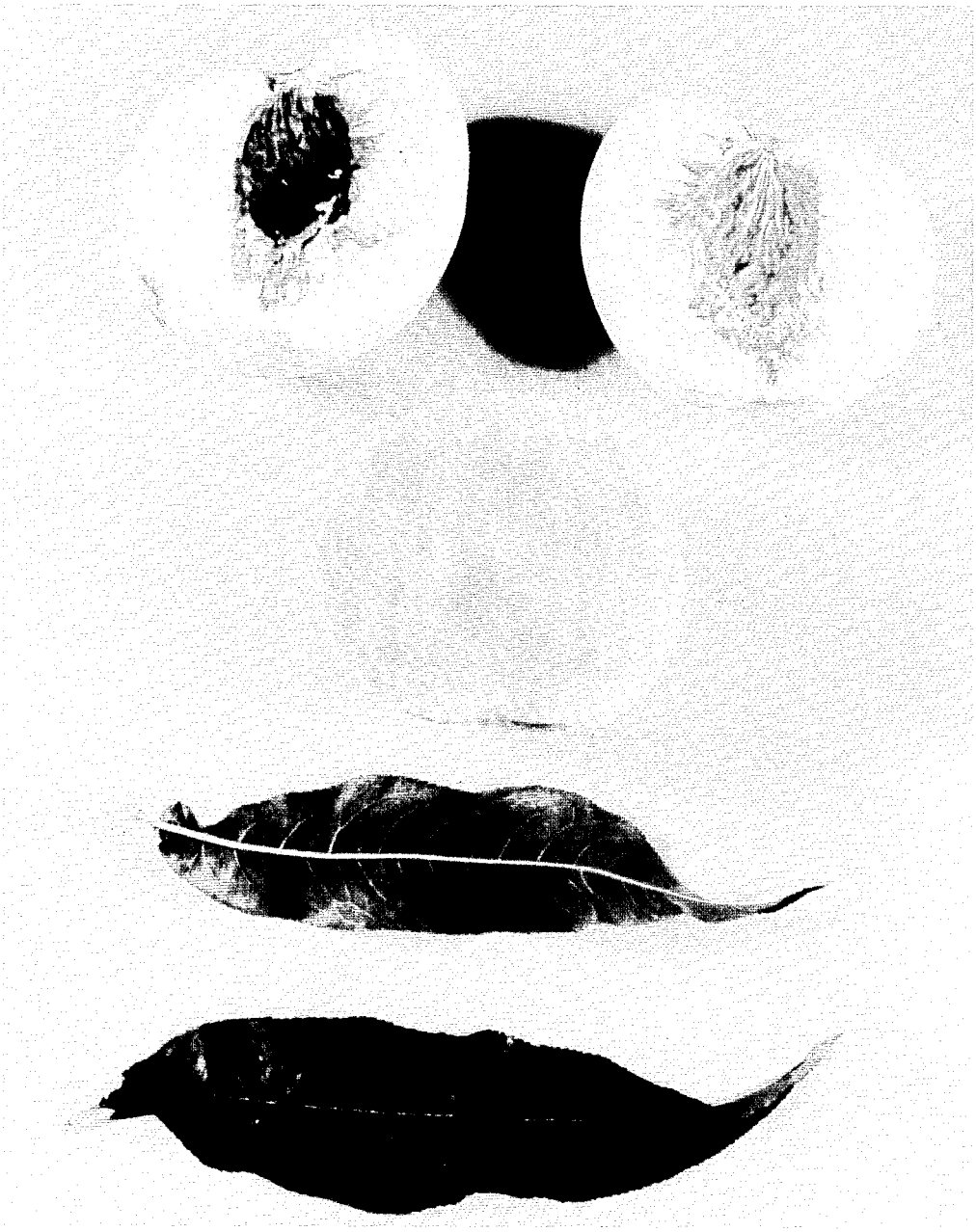
INVENTORS
WILTON L. STAGGS
SAM E. STAGGS
BY Bailey + Dority
ATTORNEYS

United States Patent Office

Plant Pat. 3,127
Patented Apr. 18, 1972

3,127

PEACH TREE

Wilton L. Staggs and Sam E. Staggs, both of Rte. 2, Campobello, S.C. 29322

Filed June 14, 1967, Ser. No. 646,133
Int. Cl. A01h *5/03*
U.S. Cl. Plt.—43 1 Claim

This invention relates to a new and distinct variety of peach tree.

The fruit of the new and distinct variety of peach tree is characterized especially by its excellent size, attractive color, and delicious flavor. The fruit is firm and fully colored with excellent shipping qualities. The fruit of this variety of tree ripens between the Loring (unpatented) and the Blake (unpatented). The fruit has an attractive ground color which is similar to the Loring, but with more bright red overcoat of both the ground coloring and the cheek coloring. This fruit possesses a somewhat brighter and livelier red color than is possessed by the Blake. The fruit of this tree represents a midseason peach of superior quality and appearance.

The new variety of peach tree was found by us as what is thought to be a chance seedling in our cultivated orchard located four miles west of Campobello, County of Spartanburg, and State of South Carolina. The tree has been asexually reproduced by us by bud grafting on seedlings from can house pits on the premises of Gramling Nursery, McMinnville, Tenn. Such asexual reproductions at maturity and when in bearing, have been found to run true to the parent tree in all respects.

The accompanying drawing, in the form of a photograph, shows typical specimens of the leaves and fruit of our new variety of peach tree with the upper and lower surfaces of the leaves being illustrated and with both exterior and sectional views of the fruit being shown, all depicted in color as nearly true as it is reasonably possible to make the same in a color illustration of this character.

The following is a detailed description of the characteristics of our new variety as based upon observations of specimens grown on the premises of Gramling Nurseries at McMinnville, Tenn., referred to above, with color terminology in accordance with Munsell's Book of Color, Munsell Color Company, Baltimore, Md., 1929–1960, except where general color terms of ordinary dictionary significance are obvious.

Tree:
- *Size.*—Medium.
- *Vigor.*—Medium.
- *Growth.*—Spreading to upright.
- *Density.*—Medium to sparse.
- *Form.*—Globular to flat.
- *Hardiness.*—Average.
- *Production.*—Average to good.
- *Bearing.*—Regular.

Trunk:
- *Size.*—Medium.
- *Texture.*—Medium to roughened.

Branches:
- *Size.*—Average.
- *Texture.*—Smooth to medium.
- *Color.*—Grayish with brown undercolor.
- *Lenticels.*—Numerous and small horizontal.

Leaves:
- *Size.*—Medium to large. Average length 6⅝″ to 7″. Average width 1½″ to 2″.

- *Form.*—Base angle obtuse; apex acute.
- *Thickness.*—Medium.
- *Texture.*—Slightly wavy and crinkled.
- *Margin.*—Serrate.
- *Petiole.*
- *Glands.*—Reinform—usually two opposite, occasionally one and three occurring at base of leaf.
- *Stipules.*—Inconspicuous.
- *Color.*—Top hue 7.5GY3/4. Underside 5GY5/4.

Flower buds:
- *Hardiness.*—Average.
- *Size.*—Medium.
- *Length.*—Elongated—medium.
- *Form.*—Long conical.
- *Pubescence.*—Medium to heavy.

Flowers:
- *Blooming period.*—Earlier than Elberta.
- *Size.*—Medium to large—slightly showy.
- *Color.*—Medium pink.

Fruit:
- *Maturity when described.*—Eating ripe.
- *First picking.*—July 21, 1966.
- *Last picking.*—August 4, 1966.
- *Size.*—Medium to large, fairly uniform.
- *Form.*—Oblate to truncate in longitudinal plane. Oblate to round in transverse plane.
- *Suture.*—Distinct, extending beyond apex with depression beyond pistil point.
- *Ventral surface.*—Rounded.
- *Cavity.*—Long, broad and deep.
- *Base.*—Round to flat.
- *Apex.*—Short, flat.
- *Pistil point.*—Depressed.

Skin:
- *Thickness.*—Medium to slightly thick.
- *Texture.*—Medium.
- *Tendency to crack.*—Very little.
- *Down.*—Light and very short.
- *Color.*—Cheek hue 7.5%5/10. Ground hue 2.5Y3/12.

Flesh:
- *Juice.*—Medium to slightly dry.
- *Texture.*—Firm and melting.
- *Fibers.*—Very slightly fibrous.
- *Ripens.*—Evenly.
- *Flavor.*—Slightly acid with full bodied flavor.
- *Aroma.*—Average.
- *Eating quality.*—Excellent.
- *Color.*—Hue 2.5Y8/10.
- *Surface of pit cavity.*—Light red with pinkish red fibers.

Stone:
- *Type.*—Free.
- *Size.*—Medium to large, average 1¾″ to 2″. Average breadth 1⅛″ to 1¼″. Average thickness ¾″ to 1″.
- *Form.*—Elliptical to obovate.
- *Base.*—Medium.
- *Sides.*—Unequal.
- *Surface.*—Pit grooves, complete surface furrowed.
- *Ridges.*—Mostly pointed and rounded to base but sometimes ending at side.
- *Pits.*—Elongated.
- *Tendency to split.*
- *Color.*—Hue 5R5/8.

The tree and its fruit herein described may vary in slight detail due to climatic and soil conditions under which the variety may be grown.

What is claimed is:

1. A new and distinct variety of peach tree substantially as shown and described characterized particularly as to novelty by its outstanding fruit which ripens at midseason between the Loring peach and the Blake peach with firm fully colored fruit with excellent shipping qualities being of excellent size, attractive color and good flavor.

No references cited.

ROBERT E. BAGWILL, Primary Examiner